(12) United States Patent
Harel et al.

(10) Patent No.: US 9,072,310 B2
(45) Date of Patent: Jul. 7, 2015

(54) DRY FOOD PRODUCT CONTAINING LIVE PROBIOTIC

(71) Applicant: Advanced BioNutrition Corporation, Columbia, MD (US)

(72) Inventors: Moti Harel, Pikesville, MD (US); Alicia Bennett, Rosedale, MD (US)

(73) Assignee: ADVANCED BIONUTRITION CORPORATION, Columbia, MD (US)

( * ) Notice: Subject to any disclaimer, the term of this patent is extended or adjusted under 35 U.S.C. 154(b) by 0 days.

(21) Appl. No.: 13/911,636

(22) Filed: Jun. 6, 2013

(65) Prior Publication Data

US 2013/0287896 A1 Oct. 31, 2013

Related U.S. Application Data

(63) Continuation of application No. 12/519,860, filed as application No. PCT/US2007/087771 on Dec. 17, 2007, now Pat. No. 8,460,726.

(60) Provisional application No. 60/875,475, filed on Dec. 18, 2006.

(51) Int. Cl.
| | |
|---|---|
| A23K 1/00 | (2006.01) |
| A23K 1/16 | (2006.01) |
| A23K 1/18 | (2006.01) |
| A23L 1/00 | (2006.01) |
| A23L 1/30 | (2006.01) |
| A23L 3/40 | (2006.01) |

(52) U.S. Cl.
CPC ............... *A23K 1/009* (2013.01); *A23K 1/004* (2013.01); *A23K 1/1631* (2013.01); *A23K 1/164* (2013.01); *A23K 1/1643* (2013.01); *A23K 1/1853* (2013.01); *A23K 1/188* (2013.01); *A23L 1/002* (2013.01); *A23L 1/0055* (2013.01); *A23L 1/3014* (2013.01); *A23L 3/40* (2013.01); *A23V 2002/00* (2013.01); *A23V 2300/10* (2013.01); *A23Y 2220/73* (2013.01); *A23Y 2300/49* (2013.01)
USPC ........................................................ 426/61

(58) Field of Classification Search
CPC ............................... A23K 1/009; A23L 1/3014
USPC ........................................................ 426/61
See application file for complete search history.

(56) References Cited

U.S. PATENT DOCUMENTS

| | | |
|---|---|---|
| 3,241,977 A | 3/1966 | Mitchell |
| 3,897,307 A | 7/1975 | Porubcan |
| 4,337,242 A | 6/1982 | Markus |
| 4,656,767 A | 4/1987 | Tarrant |
| 5,227,373 A | 7/1993 | Alexander |
| 5,262,187 A | 11/1993 | Hahn |
| 5,407,957 A | 4/1995 | Kyle et al. |
| 5,518,918 A | 5/1996 | Barclay |
| 5,637,494 A | 6/1997 | King |
| 5,658,767 A | 8/1997 | Kyle |
| 5,715,774 A | 2/1998 | Adey et al. |
| 5,731,006 A | 3/1998 | Akiyama et al. |
| 5,766,520 A | 6/1998 | Bronshtein |
| 5,908,622 A | 6/1999 | Barclay |
| 5,958,455 A | 9/1999 | Roser et al. |
| 5,968,569 A * | 10/1999 | Cavadini et al. ................ 426/61 |
| 5,981,719 A | 11/1999 | Woiszwillo et al. |
| 6,060,050 A * | 5/2000 | Brown et al. ................ 424/93.3 |
| 6,187,330 B1 | 2/2001 | Wang et al. |
| 6,190,701 B1 | 2/2001 | Roser |
| 6,258,362 B1 | 7/2001 | Loudon |
| 6,267,958 B1 | 7/2001 | Andya et al. |
| 6,290,991 B1 | 9/2001 | Roser et al. |
| 6,306,345 B1 | 10/2001 | Bronshtein et al. |
| 6,331,310 B1 | 12/2001 | Roser et al. |
| 6,338,856 B1 | 1/2002 | Allen et al. |
| 6,338,866 B1 | 1/2002 | Criggall et al. |
| 6,451,567 B1 | 9/2002 | Barclay |
| 6,468,782 B1 | 10/2002 | Tunnacliffe |
| 6,503,411 B1 | 1/2003 | Franks |
| 6,509,146 B1 | 1/2003 | Bronshtein |
| 6,509,178 B1 | 1/2003 | Tanaka et al. |
| 6,534,087 B2 | 3/2003 | Busson |
| 6,537,666 B1 * | 3/2003 | Bronshtein ................ 428/402.2 |
| 6,565,871 B2 | 5/2003 | Roser et al. |
| 6,582,941 B1 | 6/2003 | Yokochi et al. |
| 6,586,006 B2 | 7/2003 | Roser et al. |

(Continued)

FOREIGN PATENT DOCUMENTS

| | | |
|---|---|---|
| CN | 101287449 | 10/2008 |
| EP | 0259739 | 3/1988 |

(Continued)

OTHER PUBLICATIONS

Office Action for Patent Application JP 2009-541634 mailed Jun. 25, 2012 (with English translation).

Anderson, J.W., Johnstone, B.M. and Remley, D.T. (1999). Breastfeeding and cognitive development: a meta-analysis [see comments]. Am J Clin Nutr, 70, 525-35.

Grinstead G, Tokach M, Dritz S, Goodband R, Nelssen J (2000) Effects of *Spirulina platensis* on growth performance of weanling pigs. Animal Feed Sci Technol 83:237-247.

(Continued)

*Primary Examiner* — Hamid R Badr
(74) *Attorney, Agent, or Firm* — RatnerPrestia

(57) ABSTRACT

The disclosure relates to a probiotic delivery system that can be consumed as a snack-food or added to a food product. In particular, the disclosure describes a crisp and tasty treat that comprises viable probiotic microorganisms preserved in a vacuum dried matrix of sugars, proteins, and polysaccharides. The probiotic remain viable within the treat for a longer time without the need for additional moisture barrier coating. The probiotic also remain viable in the animal gastrointestinal tract.

19 Claims, 4 Drawing Sheets

(56) References Cited

U.S. PATENT DOCUMENTS

| | | | |
|---|---|---|---|
| 6,589,560 B2 | 7/2003 | Foster | |
| 6,664,099 B1 | 12/2003 | Worrall | |
| 6,716,460 B2 | 4/2004 | Abril | |
| 6,726,934 B1 | 4/2004 | Prokop | |
| 6,733,759 B2 | 5/2004 | Ivey | |
| 6,790,453 B2 | 9/2004 | Porzio et al. | |
| 6,797,266 B2 * | 9/2004 | Naidu | 424/93.45 |
| 6,811,792 B2 | 11/2004 | Roser et al. | |
| 6,872,357 B1 | 3/2005 | Bronshtein et al. | |
| 6,884,866 B2 | 4/2005 | Bronshtein | |
| 6,900,173 B2 | 5/2005 | Martin | |
| 6,919,172 B2 | 7/2005 | DePablo et al. | |
| 6,964,771 B1 | 11/2005 | Roser et al. | |
| 7,005,280 B2 | 2/2006 | Barclay | |
| 7,052,719 B2 | 5/2006 | Bernstein et al. | |
| 7,056,495 B2 | 6/2006 | Roser et al. | |
| 7,122,370 B2 | 10/2006 | Porubcan | |
| 7,153,472 B1 | 12/2006 | Bronshtein | |
| 7,258,873 B2 | 8/2007 | Truong-Le | |
| 7,282,194 B2 | 10/2007 | Sung et al. | |
| 7,381,425 B1 | 6/2008 | Truong-Le | |
| 7,396,548 B2 | 7/2008 | Kyle | |
| 7,744,925 B2 | 6/2010 | Roser et al. | |
| 7,842,310 B2 | 11/2010 | Hwang | |
| 7,927,858 B2 | 4/2011 | Mayeresse | |
| 8,097,245 B2 | 1/2012 | Harel | |
| 8,460,726 B2 | 6/2013 | Harel | |
| 8,834,951 B2 | 9/2014 | Harel | |
| 2001/0012610 A1 | 8/2001 | Bronshtein | |
| 2001/0016220 A1 | 8/2001 | Jager | |
| 2002/0192202 A1 | 12/2002 | Naidu | |
| 2003/0017192 A1 | 1/2003 | Kanafani | |
| 2003/0022333 A1 | 1/2003 | Bronshtein | |
| 2003/0165472 A1 * | 9/2003 | McGrath et al. | 424/93.4 |
| 2004/0038825 A1 | 2/2004 | Leland | |
| 2004/0047881 A1 | 3/2004 | Kyle | |
| 2004/0081638 A1 | 4/2004 | Kyle | |
| 2004/0175389 A1 * | 9/2004 | Porubcan | 424/184.1 |
| 2004/0177392 A1 | 9/2004 | Barratt et al. | |
| 2004/0219206 A1 | 11/2004 | Roser et al. | |
| 2004/0241313 A1 | 12/2004 | Nana | |
| 2005/0019417 A1 | 1/2005 | Ko et al. | |
| 2005/0032192 A1 | 2/2005 | Vesey et al. | |
| 2005/0079244 A1 | 4/2005 | Giffard | |
| 2005/0100559 A1 | 5/2005 | Myatt | |
| 2005/0153018 A1 | 7/2005 | Ubbink et al. | |
| 2005/0241011 A1 | 10/2005 | Allnut | |
| 2005/0266069 A1 | 12/2005 | Simmons | |
| 2006/0008861 A1 | 1/2006 | Allnutt | |
| 2006/0024404 A1 | 2/2006 | Kyle | |
| 2006/0120999 A1 | 6/2006 | Dhar et al. | |
| 2006/0121468 A1 | 6/2006 | Allnutt et al. | |
| 2006/0127453 A1 | 6/2006 | Harel | |
| 2006/0130162 A1 | 6/2006 | Kyle et al. | |
| 2006/0147500 A1 | 7/2006 | Klingeberg | |
| 2006/0222694 A1 | 10/2006 | Oh | |
| 2006/0258623 A1 | 11/2006 | Harel | |
| 2006/0265766 A1 | 11/2006 | Kyle | |
| 2007/0020289 A1 | 1/2007 | Mattern | |
| 2007/0031534 A1 | 2/2007 | Tsujimoto | |
| 2007/0082008 A1 | 4/2007 | Harel et al. | |
| 2007/0292952 A1 | 12/2007 | Dhar et al. | |
| 2008/0044081 A1 | 2/2008 | Lieb | |
| 2008/0044481 A1 | 2/2008 | Harel | |
| 2008/0050497 A1 | 2/2008 | Mai | |
| 2008/0102132 A2 | 5/2008 | Giner | |
| 2008/0131514 A1 | 6/2008 | Truong-Le | |
| 2008/0193546 A1 | 8/2008 | Roser | |
| 2008/0194504 A1 | 8/2008 | Kyle et al. | |
| 2008/0229609 A1 | 9/2008 | Bronshtein | |
| 2008/0241244 A1 | 10/2008 | Truong-Le | |
| 2008/0261916 A1 | 10/2008 | Jaszberenyi | |
| 2009/0155351 A1 | 6/2009 | Hejl | |
| 2009/0162521 A1 | 6/2009 | Clinger | |
| 2009/0181363 A1 | 7/2009 | Dhar | |
| 2009/0203592 A1 | 8/2009 | Beermann | |
| 2009/0208585 A1 | 8/2009 | Roser et al. | |
| 2009/0232894 A1 | 9/2009 | Chouvenc | |
| 2009/0238890 A1 | 9/2009 | Piechocki | |
| 2009/0246184 A1 | 10/2009 | Harel | |
| 2009/0324636 A1 | 12/2009 | Piechocki | |
| 2010/0015177 A1 | 1/2010 | Drew | |
| 2010/0047393 A1 | 2/2010 | Glas | |
| 2010/0074994 A1 | 3/2010 | Harel | |
| 2010/0086638 A1 | 4/2010 | Kyle | |
| 2010/0092521 A1 | 4/2010 | Dhar | |
| 2010/0120014 A1 | 5/2010 | Bronshtein | |
| 2010/0120676 A1 | 5/2010 | Boehm | |
| 2010/0189767 A1 | 7/2010 | Shimoni | |
| 2010/0297231 A1 | 11/2010 | Vehring | |
| 2011/0070334 A1 | 3/2011 | Rangavajla | |
| 2012/0009248 A1 | 1/2012 | Truong-Le | |
| 2012/0039956 A1 | 2/2012 | Harel | |
| 2012/0040010 A1 | 2/2012 | Harel | |
| 2012/0114621 A1 | 5/2012 | Harel | |
| 2012/0288483 A1 | 11/2012 | Harel | |
| 2012/0322663 A1 | 12/2012 | Harel | |
| 2013/0287896 A1 | 10/2013 | Harel | |
| 2013/0296165 A1 | 11/2013 | Harel | |

FOREIGN PATENT DOCUMENTS

| | | |
|---|---|---|
| EP | 0471904 | 2/1992 |
| EP | 1 110 462 | 6/2001 |
| EP | 1 344 458 | 9/2003 |
| GB | 1232057 | 5/1971 |
| GB | 2 389 787 | 12/2003 |
| JP | 05246856 | 9/1993 |
| JP | 06022746 | 2/1994 |
| JP | 11506467 | 6/1999 |
| JP | 11513700 | 11/1999 |
| JP | 2001505431 | 4/2001 |
| JP | 2004506437 | 3/2004 |
| JP | 2004-525106 | 8/2004 |
| JP | 2004-528288 | 9/2004 |
| JP | 2005-501268 | 1/2005 |
| JP | 2005-519600 | 7/2005 |
| JP | 2005270100 | 10/2005 |
| JP | 2007522085 | 8/2007 |
| JP | 2009522280 | 6/2009 |
| JP | 2010512755 | 4/2010 |
| KR | 20050105669 | 11/2005 |
| KR | 1020050106559 | 11/2005 |
| WO | 9640077 | 12/1996 |
| WO | 9824327 | 6/1998 |
| WO | 9824882 | 6/1998 |
| WO | 0112779 | 2/2001 |
| WO | 0136590 | 5/2001 |
| WO | 0215720 | 2/2002 |
| WO | 02061111 | 8/2002 |
| WO | WO 02/058735 | 8/2002 |
| WO | WO 02/076391 | 10/2002 |
| WO | WO 03/088755 | 10/2003 |
| WO | WO 03/089579 | 10/2003 |
| WO | WO 03/103692 | 12/2003 |
| WO | 2004039417 | 5/2004 |
| WO | WO 2004/043139 | 5/2004 |
| WO | 2004080196 | 9/2004 |
| WO | 2004091307 | 10/2004 |
| WO | 2004112767 | 12/2004 |
| WO | WO 2004/112776 | 12/2004 |
| WO | WO 2005/030229 | 4/2005 |
| WO | 2005060937 | 7/2005 |
| WO | 2005084646 | 9/2005 |
| WO | 2005105978 | 11/2005 |
| WO | 2005117962 | 12/2005 |
| WO | WO 2006/122299 | 11/2006 |
| WO | 2007035455 | 3/2007 |
| WO | 2007038926 | 4/2007 |
| WO | WO 2007/067207 | 6/2007 |
| WO | 2007084059 | 7/2007 |
| WO | WO 2007/075988 | 7/2007 |
| WO | WO 2007/079147 | 7/2007 |
| WO | WO 2007/084500 | 7/2007 |

(56) References Cited

FOREIGN PATENT DOCUMENTS

| WO | 2007117511 | 10/2007 |
|---|---|---|
| WO | 2007136553 | 11/2007 |
| WO | WO 2008/016214 | 2/2008 |
| WO | 2008056983 | 5/2008 |
| WO | 2008076975 | 6/2008 |
| WO | 2009002481 | 12/2008 |
| WO | 2009140327 | 11/2009 |
| WO | 2010002418 | 1/2010 |
| WO | 2010111347 | 9/2010 |
| WO | 2010118188 | 10/2010 |
| WO | 2010118205 | 10/2010 |
| WO | 2010135495 | 11/2010 |
| WO | 2010138522 | 12/2010 |
| WO | 2011094469 | 8/2011 |

OTHER PUBLICATIONS

He ML, Hollwich W, Rambeck WA (2002) Supplementation of algae to the diet of pigs: a new possibility to improve the iodine content in the meat. J Animal Physiol Animal Nutri 86:97-104.

Ikemoto, A., Kobayashi, T., Watanabe, S. and Okuyama, H. (1997). Membrane fatty acid modifications of PC12 cells by arachidonate or docosahexaenoate affect neurite outgrowth but not norepinephrine release. Neurochem Res, 22, 671-8.

Stordy, BJ. (1995). Benefit of docosahexaenoic acid supplements to dark adaptation in dyslexics [letter; comment]. Lancet, 346, 385.

Xu, L.Z., Sanchez, R., SaIi, A. and Heintz, N. (1996). Ligand specificity of brain lipid-binding protein. J Biol Chem, 271, 24711-9.

Bazan, N.G. and Scott, B. L. (1990). Dietary omega-3 fatty acids and accumulation of docosahexaenoic acid in rod photoreceptor cells of the retina and at synapses. Ups J Med Sci Suppl, 48, 97-107.

Bazan, N.G. and Rodriguez de Turco, E.B. (1994). Review: pharmacological manipulation of docosahexaenoic-phospholipid biosynthesis in photoreceptor cells: implications in retinal degeneration. J Ocul Pharmacol, 10, 591-604.

Behrens, P. and Kyle, D. (1996). Microalgae as a source of fatty acids. J Food Sci, 3, 259-272.

Boswell KDB, Gladue R, Prima B, Kyle DJ (1992) SCO production by fermentive microalgae. In: Kyle DJ, Ratledge C (eds) Industrial Applications of Single Cell Oils. American Oil Chemists Society, Champaign. IL., pp. 274-286.

Crawford, M.A., Costeloe, K., Ghebremeskel, K. and Phylactos, A. (1998). The inadequacy of the essential fatty acid content of present preterm feeds [published erratum appears in Eur J Pediatr Feb. 1998;157(2):160]. Eur J Pediatr, 157 Suppl 1, S23-7.

Martinez, M. (1990). Severe deficiency of docosahexaenoic acid in peroxisomal disorders: a defect of delta 4 desaturation. Neurology, 40, 1292-8.

Salem, N.J., Kim, H-Y., and Yergey, J.A. (1986). Docosahexaenoic acid: membrane function and metabolism. In Health Effects of Polyunsaturated Fatty Acids in Seafoods pp. 263-317. Academic Press, Inc.

Anal et al. "Recent advances in microencapsulation of probiotics for industrial applications and targeted delivery." Trends in Food Science and Technology, vol. 18, No. 5, Apr. 29, 2007, pp. 240-251.

Krasaekoopt et al. "Evaluation of encapsulation techniques of probiotics for yoghurt." International Dairy Journal, 2003. pp. 3-13.

Abdelwahed et al., Advanced Drug Delivery Reviews, 58:1688-1713 (2006).

Annear, D., "The preservation of leptospires by drying from the liquid state," Journal of General Microbiology, 27 (1962) 341-343.

Bergogne et al., Molecular Crystals and Liquid Crystals, 354: 79-89 (2000).

Capela, P., et al., "Effect of cryoprotectants, prebiotics and microencapsulation on survival of probiotic organisms in yoghurt and freeze-dried yoghurt," Food Research International, 39 (2006) 203-211.

Chen, et al., "Beneficial Effect of Intracellular Trehalsose on the Membrane Integrity of Dried Mammalian Cells", Cryobiology vol. 43, pp. 168-181, 2001.

Chen et al., China Tropical Medicine, 7(4):654-55 (2007) (with partial English translation).

Chinese Search Report dated May 26, 2014 for application No. 201180039219.7 filed Aug. 12, 2011.

Crowe, J.H., Crowe., L.M., and Mouriadian, R., 1983, Cryobiology, 20, 346-356.

Crowe et al., "Anhydrobiosis: A Strategy for Survival", Adv. Space Res vol. 12, No. 4, pp. 239-247, 1992.

De Giulio, et al., "Use of alginate and cryo-protective sugars to improve the viability of lactic acid and bacteria after freezing and freeze-drying", World Journal of Microbiology and Biotechnology, Kluwer Academic Publishers, DO, vol. 21, No. 5, Jul. 1, 2005, pp. 739-746.

Desai et al., Pharmaceutical Research, 13(12):1838-45 (1996).

Entire patent prosecution history of U.S. Appl. No. 12/519,860, filed Dec. 2, 2009, entitled, "Dry Food Product Containing Live Probiotic," now U.S. Patent No. 8,460,726.

Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Patent No. 8,097,245.

Entire prosecution history of U.S. Appl. No. 13/208,459, filed Aug. 12, 2011, entitled, "Dry Storage Stabilizing Composition for Biological Materials."

Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making."

Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same."

Entire prosecution history of U.S. Appl. No. 13/378,106, filed Mar. 29, 2012, entitled, "Dry Glassy Composition Comprising a Bioactive Material," now U.S. Patent No. 8,834,951.

Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same."

Entire prosecution history of U.S. Appl. No. 13/849,941, filed Mar. 25, 2013, entitled Stablizing Composition for Biological Materials.

Entire prosecution history of U.S. Appl. No. 14/456,130, filed Aug. 11, 2014, entitled, "Dry Glassy Composition Comprising a Bioactive Material."

Entire prosecution history of U.S. Appl. No. 14/479,791, filed Sep. 8, 2014, entitled, "Dry Food Product Containing Live Probiotic."

Esquisabel et al., 1997, J. Microencapsulation, 14, 627-638.

Favaro-Trindade et al., "Microencapsulation of L. acidophilus (La-05) and B. lactis (Bb-12) and evaluation of their survival at the pH values of the stomach and in bile", J. Microencapsulation, vol. 19, pp. 485-494, 2002.

First Office Action with a Search Report issued by the State Intellectual Property Office of the People\s Republic of China on May 22, 2013 for Chinese Application No. 201180007562.3.

Hincha, D., et al., "Protection of liposomes against fusion during drying by oligosaccharides is not predicted by the calorimetric glass transition temperatures of the dry sugars," European Biophysics Journal, 37 (2008) 503-508.

International Preliminary Report on Patentability for PCT International Application No. PCT/US2011/022821 dated Jul. 31, 2012.

Inulin, Shin et al., Growth and Viability of Commerical Bifidobacterium spp in Skim Milk containing oligosaccharides and Inulin, Journal of Food Microbiology and Safety, 2000, vol. 65, No. 5.

Japanese Office Action issued in related Japanese Application No. 2013-524242, dated Jan. 21, 2014.

Japanese Office Action mailed Aug. 1, 2014 in corresponding Japanese Application No. 2012-513183, with translation.

Kailasapathy et al., "Survival and therapeutic potential of probiotic organisms with reference to *Lactobacillus acidophilus* and Bifidobacterium spp.," Immunology Cell Biology, 78, pp. 80-88, 2000.

(56) References Cited

OTHER PUBLICATIONS

Kearney, et al., "Enhancing the Viability of *Lactobacillus plantarum* Inoculum by Immobilizing the Cells in Calcium-Alginate Beads Incorporation Cryoprotectants", Applied and Environmental Microbiology, vol. 56, No. 10, Oct. 1990, pp. 3112-3116.
Kets et al, "Citrate increases glass transition temperature of vitrified sucrose preparations," Cryobiology 48 (2004), 46-54.
Krallish et al., "Effect of xylitol and trehalose on dry resistance of yeasts", Appl. Microbiol Biotechnol. 47, pp. 447-451, 1997.
Liao et al., "Protective Mechanism of Stabilizing Excipients against Dehydration in the Freeze-Drying of Proteins", Pharmaceutical Research, vol. 19, No. 12, pp. 1854-1861, 2002.
Linders et al., "Effect of Added Carbohydrates on Membrane Phase Behavior and Survival of Dried *Lactobacillus plantarum*", Cryobiology 35, pp. 31-40, 1997.
M. Le Meste, et al., 2002, Glass Transition and Food Technology: A Critical Appraisal, Journal of Food Science, 67:2444-2458.
Marteau et al., "Protection from gastrointestinal diseases with the use of probiotics", Am J Clin Nutr. 73, pp. 430S-436S, 2001.
Mazur et al., "Hydration of Sodium Alginate in Aqueous Solution, Macromolecules, ACS Publications, Nov. 18, 2013.
Morgan, C., et al., "Preservation of micro-organisms by drying; a review," Journal of Microbiological Methods, 66 (2006) 183-193.
New Zealand Examination Report dated May 18, 2012.
Niness, Inulin and Olgifructose: What are they?., J. Nutr. 129, 1999.
Office Action dated Mar. 21, 2014 in corresponding Russian patent application, with translation.
Office Action mailed Aug. 6, 2014 in corresponding Russian Application No. 2011151788/10(077759).
Perdigon et al, "Lactic Acid Bacteria and their Effect on the Immune System", Curr Issues Intest Microbiol. 2, pp. 27-42, 2001.
Qiu et al., "Permeability of the infective juveniles of Steinernema carpocapsae to glycerol during osmotic dehydration and its effect on biochemical adaptation and energy metabolism", Comparative Biochemistry & Physiology, Part B, vol. 125, pp. 411-419, 2000.
Sanchez et al., 1999, Intl. J. Pharm. 185, 255-266.
Schwab, C., et al., "Influence of oligosaccharides on the viability and membrane properties of *lactobacillus reuteri* TMW1.106 during freeze-drying," Cryobiology, 55 (2007) 108-114.
Second Examination Report issued in related Chilean Application No. 01984-2011, dated Jan. 24, 2014.
Second Office Action issued by the State Intellectual Property Office of the People\s Republic of China Feb. 8, 2014 in corresponding Chinese Application No. 20140129900353490, including a Search Report (with English translation).
Selmer-Olsen, et al., "Survival of *Lactobacillus* helveticus entrapped in Ca-alginate in relation to water content, storage and rehydration", Journal of Industrial Microbiology & Biotechnology, vol. 23, 1999, pp. 79-85.
Substantive Examination Adverse Report mailed Aug. 29, 2014 in counterpart Malaysian Application No. PI 2011005733.
Sucrose, Sucrose structure, Webpage, Elmhurst College, 2003.
Supplementary European Search report corresponding with Application No. EP 10 78 1100 dated Sep. 28, 2012.
Supplementary European Search Report for European Appln No. 11737688.9 dated Sep. 18, 2013.
Sutas et al., "Probiotics: effects on immunity", Am J Clin Nutr. 73, pp. 444S-450S, 2001.
Tobar et al., Oral Vaccination of Atlantic Salmon Salmo salar against Salmon Rickettsial Septicaemia, presentation, World Aquaculture Society\s 2008 annual international conference (May 19-23, 2008).
Tobar et al., Oral Vaccination of Atlantic Salmon Salmo salar against Salmonid rickettsial septicaemia (SRS), abstract, World Aquaculture Society\s 2008 annual international conference (May 19-23, 2008).
Translation of Japanese Office Action for Japanese Patent Application No. 2008-548729, mailed Jul. 23, 2012.
Wong, Recent Patents on Drug Delivery & Formation 3:1720-23 (2009).
Young, Lee W., International Search Report for International Application No. PCT/US2006/49434 dated Sep. 26, 2007.
Zarate et al ("Viability and biological properties of probiotic vaginal lactobacilli after lyophilization and refrigerated storage into gelatin capsules," Process Biochemistry 41 (2006), 1779-1785.
Canadian Office Action mailed Apr. 6, 2011 in counterpart Canadian Application No. 2,673,120.
International Search Report for corresponding International Application No. PCT/US2007/087771 mailed May 16, 2008.
Crowe, J.H., Carpenter, J.F., and Crowe, L.M. (1998). "The role of vitrification in anhydrobiosis. Review." Arum Rev Physiol. 60:73-103.
Hughes, V.X. and Hillier, S.L. (1990). "Microbiologic characteristics of *Lactobacillus* products used for colonization of the vagina." Obstet Gynecol.
Shah, N.P. (2000). "Probiotic bacteria: selective enumeration and survival in dairy foods." Journal of Dairy Science. 83:894-907.
Notice of Allowance mailed Oct. 27, 2014 in U.S. Appl. No. 13/459,408.
Office Action mailed Oct. 27, 2014 in U.S. Appl. No. 13/208,459.
International Preliminary Report on Patentability and Written Opinion for PCT International Application No. PCT/US2013/033505 issued Sep. 23, 2014.
Canadian Office Action mailed Oct. 10, 2014 in Canadian Application No. 2,785,815.
Benedict, R.G. et al., "Preservation of Microorganisms by Freeze-Drying I. Cell Supernatant, Naylor-Smith Solution, and Salts of Various Acids as Stabilizers for Serratia marcascens," Appl. Microbiol. 1958, vol. 6, No. 6, pp. 401-407.
European Office Action for Application No. 10 781 100.2-1403 dated Oct. 17, 2014.
Extended European Search Report for European Application No. 11817090.1-1358 dated Jun. 16, 2014.
International Search Report for International Application No. PCT/US2010/036098 mailed Feb. 14, 2011.
International Search Report for International Application No. PCT/US2011/022821 mailed Oct. 25, 2011.
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Perry, Stephen F, "Freeze-Drying and Cryopreservation of Bacteria," Molecular Biotechnology, 1998, vol. 9, No. 1, pp. 59-64.
Office Action mailed Jan. 14, 2015 in U.S. Appl. No. 13/321,708.
Russian Office Action mailed Dec. 18, 2014 in Application No. 2011151788/10(077759).
Notice of Allowance mailed Feb. 9, 2015 in U.S. Appl. No. 13/351,343.

\* cited by examiner

FIG 1. Effect of each component in the composition of the present invention on viability Loss of LGG Probiotic after vacuum-drying

| LGG paste | Trehalose | Egg White | Alginate | Log Loss |
|---|---|---|---|---|
| 10% | 0% | 0% | 0% | 2.27 |
| 10% | 30% | 0% | 2% | 1.96 |
| 10% | 0% | 30% | 2% | 1.87 |
| 10% | 30% | 10% | 2% | 0.28 |

\* Component amount is in percent of water content in the composition

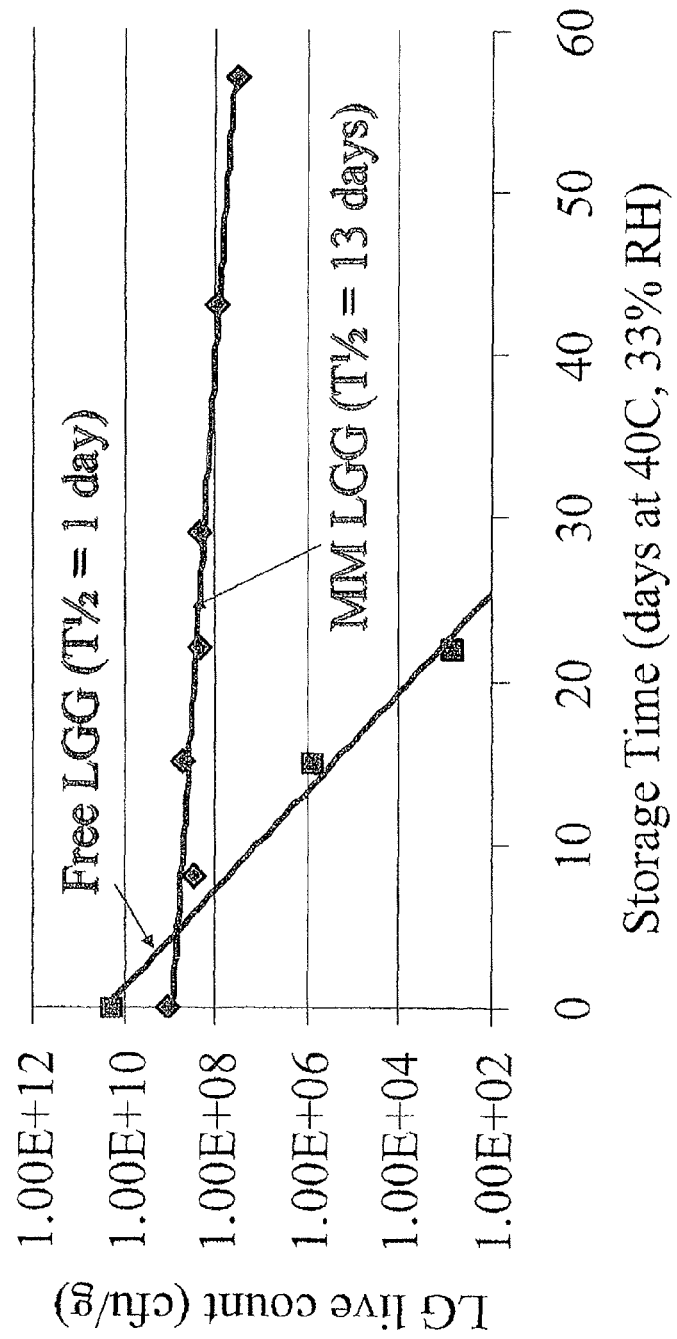
FIG 2. Shelf Life of Probiotic LGG Under Accelerated Conditions at High Temperature (40°C) and Humidity (33% RH)

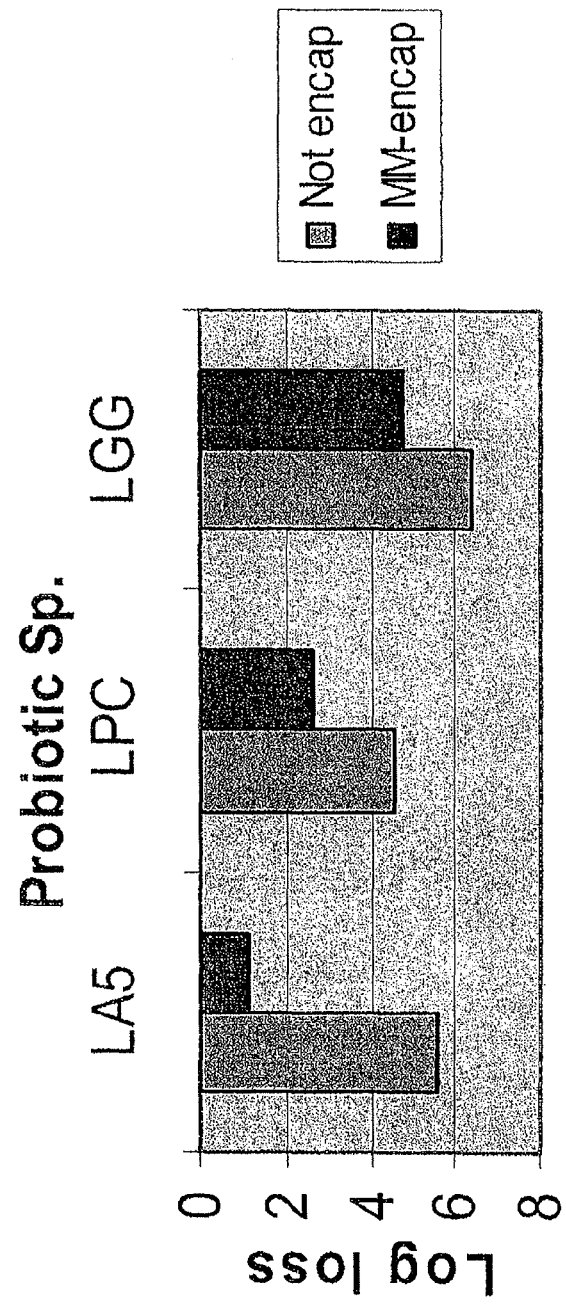
FIG 3. Gastric Loss of Probiotics, Produced as Described Herein (pH 1.2)

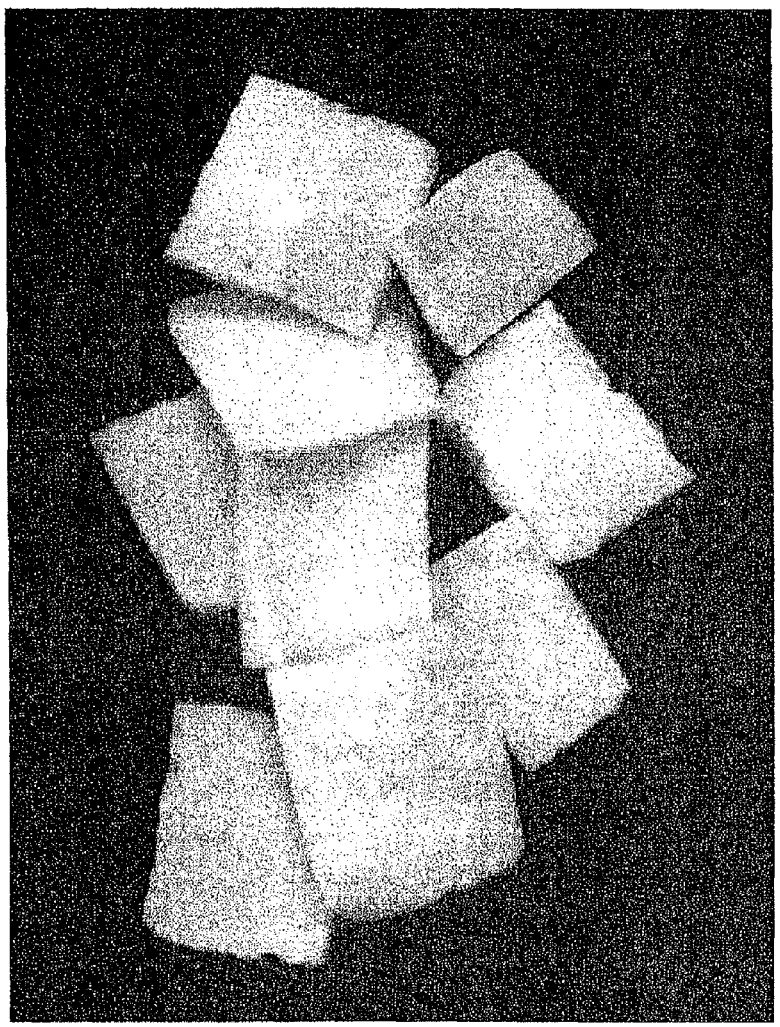
FIG 4. Examples of Probiotic Chips Produced as Described Herein

DRY FOOD PRODUCT CONTAINING LIVE PROBIOTIC

CROSS REFERENCE TO RELATED APPLICATIONS

This application is a continuation of U.S. application Ser. No. 12/519,860, filed 2 Dec. 2009, which is the National Phase filing of International Application number PCT/US07/87771, filed 17 Dec. 2007, and claims priority of U.S. Provisional Application No. 60/875,475, filed 18 Dec., 2006, the entireties of which applications are incorporated herein by reference for all purposes.

BACKGROUND OF THE DISCLOSURE

1. Field of the Invention

The disclosure relates generally to the fields of probiotics and food.

2. Related Art

The activity and long term stability of many biological materials, such as proteins, enzymes and microbial cells may be affected by a number of environmental factors; for example, temperature, pH, the presence of water and oxygen or oxidizing or reducing agents. Generally, biological materials must be dried before or during mixing with other foodstuff ingredients. The drying process can often result in a significant loss in activity from mechanical, chemical, and osmotic stresses induced by the drying process. Loss of activity occurs at many distinct stages, including drying during initial manufacturing, feed preparation (high temperature and high pressure), transportation and long term storage (temperature and humid exposure), and after consumption and passage in the gastrointestinal (GI) track (exposure to low pH, proteolytic enzymes and bile salts). Manufacturing food or feedstuffs with live cell organisms or probiotics is in particular challenging, because the probiotics are very sensitive to the drying process and to temperature and moisture conditions of the foodstuff. Another concern is the probiotic resistance in the acid environment in the stomach and its successful colonization of the intestine.

Probiotic microorganisms (probiotics) are living microorganisms, which upon ingestion in certain numbers, exert health benefits beyond basic nutrition. The beneficial effects that probiotics may induce are numerous. Few examples are; the reduction of lactose intolerance, the inhibition of pathogenic bacteria and parasites, the reduction of diarrhea, activity against *Helicobacter pylori*, the prevention of colon cancer, the improvement or prevention of constipation, the in situ production of vitamins, the modulation of blood lipids, and the modulation of host immune functions. In domesticated and aquatic animals they also can improve growth, survival and stress resistance associated with diseases and unfavorable culture conditions. Therefore, there is considerable interest in including probiotics into human foodstuffs and into animal feed.

Many probiotics exhibit their beneficial effect mainly when they are alive. Hence, they need to survive the manufacturing process and shelf life of the food, and upon consumption of the food where they need to pass through the gastro-intestinal tract before reaching their place of colonization. Although many commercial probiotic products are available for animal and human consumptions, most of them lost their viability during the manufacture process, transport, storage and in the animal GI tract (see the viability studies of several probiotic products by (Hughes and Hillier 1990; Shah 2000). To compensate for such loss, an excessive quantity of probiotics is included in the product in anticipation that a portion will survive and reach their target. In addition to questionable shelf-life viability for these products, such practices are certainly not cost-effective. Alternatively, the probiotic microorganisms can be encapsulated in protective microenvironments. Generally, current microencapsulation and enteric coating techniques involve applying a film forming substance, usually by spraying liquids containing sugars or proteins onto the dry probiotics (Ko and Ping WO 02/058735). However, coating the microencapsulated probiotics with moisture protecting layers is an expensive process, and generally several layers must be added, to avoid water entering the microcapsules. In addition, it is extremely difficult to remove the added liquid in the coating substance without a corresponding decrease in shelf life.

Various protective agents have been used in the art, with varying degrees of success. These include proteins, certain polymers, skim milk, glycerol, polysaccharides, oligosaccharides and disaccharides. Disaccharides, such as sucrose and trehalose, are particularly attractive cryoprotectants because they are actually help plants and microbial cells to remain in a state of suspended animation during periods of drought. Trehalose has been shown to be an effective protectant for a variety of biological materials, both in ambient air-drying and freeze-drying (Crowe et al. 1998). However, there are some drawbacks associated with the use of sugars as the sole cryoprotectant. For example, large amounts of sugars (often greater than 60% by weight) must be used to preserve the biological materials during the drying process. This is costly. More serious problems associated with the use of sugars include their readiness to form crystals when the material is dried below its freezing point, and the low glass transition temperature which causes instability of the preserved biological materials at high temperatures, and/or in humid environments. Further, high concentration of sugars reduces the solubility of other solutes in the system and at the same time renders the system extremely difficult to dry.

Accordingly, it has been proposed to dry sugar-based probiotic systems by foam formation in a very thin layer (Bronshtein WO2005117962), or to use combinations of sugars with a polymeric gelling agent, such as alginate, chitosan, carboxymethylcellulose or carboxyethylcellulose. Cavadini et al. (EP 0 862 863) provide a cereal product comprising a gelatinized starch matrix including a coating or a filling. The probiotic is included with the coating. According to that process, spray-dried probiotics are mixed with a carrier substrate, which may be water, fat or a protein digest. The mixture is then sprayed onto the cereal product and the whole product is dried again. Re-hydrating of the already dried bacteria and the additional coating/drying process is costly and damaging to the bacteria.

Kenneth and Liegh (U.S. Pat. No. 6,900,173) describe the manufacturing of multivitamin protein and probiotic bar for promoting an anabolic state in a person. The dried probiotic bacteria are blended in sugar syrup and several other constituents, and the resultant mixture is then extruded and cut into bars. However, the document does not disclose any process or composition that will improve viability or long-term stability of probiotics in the nutritional bars and there is no indication that the bacteria even survive the process.

Ubbink et al. (US 2005/0153018) disclose the preservation of lactic acid bacteria in moist food. The spray-dried bacteria are added to a composition comprising fats, fermented milk powder and saccharides. That composition is then used as the filling of a confectionary product. The subject matter described in that document avoids the detrimental effects of water by embedding the probiotics in fat or oil rich matrix.

However, fat based coating and preserving materials do not withstand long term exposure to humid conditions.

Giffard and Kendall (US 2005/0079244) disclose a foodstuff in the form of a dried or semi-moist ready-to-eat kibble or powder mix, which contains a combination of a probiotic, prebiotic and a coating of colostrum. Prior to mixing in the food stuff, the probiotic is coated or encapsulated in a polysaccharide, fat, starch, protein or in a sugar matrix using standard encapsulation techniques. Similar to the above disclosure, the negative effects of water were avoided by embedding the probiotics in a matrix rich in fat or oil.

Farber and Farber (WO 03/088755) describe an oral delivery system for functional ingredients uniformly dispersed in a matrix. The matrix components include a sugar, a carbohydrate, a hydrocolloid a polyhydric alcohol and a source of mono-or divalent cations. The delivery system is extruded or molded into a final shape with a moisture content of between 15% and 30% by weight. This type of matrix provides very little protection to the probiotics mostly under refrigerated conditions. No description or direction was provided as to how probiotic bacteria are stabilized during manufacturing or for prolonged storage at room temperatures.

Porubcan (US 2004/0175389) discloses a formulation for protecting probiotic bacteria during passage through the stomach, whilst permitting their release in the intestine. The formulation has also a low water activity and correspondingly long shelf life. The capsule includes a water-free mixture of probiotic bacteria with monovalent alginate salts, and an enteric coating (e.g., gelatin or cellulose encapsulation). Upon contact with acidic environment, the outer shell of the capsule turned into a gel, which provides a protecting barrier against proton influx into the capsule core. However, this composition is only useful for large particles such as tablets and capsules subjected to storage conditions of very low water activity and further require storage in nitrogen-flushed or vacuum-sealed containers. McGrath and Mchale (EP 1382241) describe a method of delivering a microorganism to an animal. The micro-organism is suspended in a matrix of cross-linked alginate and cryopreservant (trehalose or lactose, or a combination of both). The matrix is then freeze or vacuum dried to form dry beads containing live probiotics with a shelf-life stability up to 6 months but only under refrigerated conditions. Here again, no description or direction was provided as to how probiotic bacteria are stabilized during manufacturing or for prolonged storage at room temperatures and high humidity conditions.

None of the above compositions provide a mixture that can effectively protect the probiotic in both drying processes and long-term storage at elevated temperatures and varying degrees of humidity. Therefore, there is an urgent need for such a composition that can effectively protect the probiotic bacteria during manufacturing, long-term storage at elevated temperatures and humidity and during gastrointestinal passage. There is a need also for a drying process that is cost-effective and capable of entrapping and stabilizing probiotics in the protective mixture with minimal viability loss at the end of the entire operation. There is a need for a protective mixture that provides protection in the animal stomach while allowing the release of the probiotic along the intestinal tract. There is also a need for a protective mixture that contains only approved ingredients generally regarded as safe (GRAS), and is less costly than those presently being used.

The subject matter described herein overcomes these needs and provides a composition and process for producing a composition that provides probiotic bacteria that are stable for long periods of time even at elevated temperatures and varying degrees of humidity.

It is, in particular, a purpose of the present disclosure to describe viable probiotic cultures that are substantially stable at room temperature and high humidity conditions thereby obviate the need for refrigeration or storage under vacuum or oxygen free environment.

BRIEF SUMMARY OF THE DISCLOSURE

It was unexpectedly found that probiotic bacteria are protected for an extended period of time in high temperature and humid conditions when preserved in a certain protective mixture. Additional qualities of the protecting mixture are, a fast and cost effective drying process and gastric protection. The mixture comprises: (a) at least one sugar compound, where the total amount of sugar compound in the mixture is from about 10% to about 60% by weight of the mixture (b) proteins, where the total amount of proteins in the medium is from about 2% to about 20% by weight of the mixture and (c) polysaccharides, where the total amount of polysaccharides in the medium is from about 0.5% to about 5% by weight of the mixture. This aqueous protective mixture can be used in a multiplicity of preservation processes, including freezing, freeze-drying, spray-drying, vacuum-drying, or ambient air-drying, to provide a stable and preserved composition of probiotics. The probiotic substance is stable for extended periods of time at superambient temperatures and/or relative humidity. Further, the aqueous protective mixture containing the probiotics can be molded into a desirable shape or form and vacuum-dried to produce a crisp and tasty probiotic treat that can be added to food stuff or consumed on its own by humans or animals.

Therefore, the present disclosure also describes a method for preparing a preserved probiotic substances containing the above-noted protective mixture.

Preferably, the probiotic substance is provided in a dry foam that is substantially free of water. The probiotic substance maybe freeze-dried, vacuum dried or air dried, or otherwise dried by methods known in the art. Accordingly, the probiotic substance preferably comprises a protective mixture capable of maintaining the viability of the probiotic micro-organisms for extended periods of time in ambient temperature and humidity conditions.

Preferably, the sugar in the protective mixture is a disaccharide, most preferably trehalose or sucrose or lactose or a combination thereof. The protective mixture preferably comprises trehalose at 20% w/v to 60% w/v trehalose, preferably 20%, 30% or 40%.

Preferably, the protein in the protective mixture of the subject matter described herein is egg albumen or soy protein isolate or hydrolysate and a mixture thereof. The protective mixture preferably comprises proteins at 2% w/v to 20% w/v proteins, preferably 5%, 10% or 20%.

Preferably, the polysaccharides in the protective mixture described herein can form a firm gel or viscous solution with the other ingredients in the mixture, most preferably a combination of alginates with different viscosities, agarose, pectin or chitosan. The protective mixture preferably comprises alginates at 0.5% w/v to 10% w/v alginates, preferably 1%, 2% or 4%.

In accordance with the subject matter described herein, there is provided the use of the probiotic substance described herein for the manufacture of a probiotic product or a probiotic food or feed product for the consumption by humans, domestic animals, aquatic animals and pets.

Remarkably, it was found that by adding a mixture containing 30% trehalose (w/v), 10% soy protein isolate (w/v) and 2% sodium alginate to a probiotic bacteria concentrate, forming viscous solution or hydrogel and vacuum drying it at temperature above the freezing point of the mixture an excellent process recovery, prolonged stability over storage time in ambient conditions and gastric protection are obtained.

Optionally, the probiotic substance may be coated with a moisture barrier component. In principle, any food-grade substance having water repelling or impermeable properties may be selected. Suitable moisture barriers may be, for example, a mixture of oil based substances.

Consequently, in a first aspect, the subject matter described herein includes a probiotic product comprising a dry micro-matrix particle of the above mixture, wherein the micro-matrix particle comprises viable microorganisms and has a size between 10 and 2000 microns.

In a second aspect, the subject matter described herein includes a food product containing probiotic flakes or treats, wherein the flakes or treats are the probiotic substance described herein, characterized in that the flake or treat has a desirable shape and size between 2-50 millimeters.

In a third aspect, the subject matter described herein includes a process for obtaining micro-matrix particles, to supplement a food product with viable micro-organisms. The process comprises the steps of mixing micro-organisms concentrate and further protective components, forming viscous solution or hydrogel, drying the mixture by freeze-drying, spray-drying, vacuum-drying, or ambient air-drying, and, if necessary, grinding the dry material to obtain micro-matrix particles comprising a size between 50-2000 microns.

In a fourth aspect, the subject matter described herein includes a process for obtaining flakes or treats as supplement or stand-alone food product with viable microorganisms. The process comprises the steps of mixing micro-organisms concentrate and further protective components, forming a hydrogel in a desirable shape and size and drying by vacuum-drying, to obtain crispy and tasty flakes or treats comprising a size between 2-50 millimeters.

One major advantage of the subject matter described herein is that it provides a significant improvement over other drying methods of sugar based substances and production methods of stable probiotic micro-organisms in semi-dry and/or humid particulate foodstuffs.

Another advantage of the subject matter described herein is that the drying process is easy to upscale and straightforward with no need of additional coating or several drying stages.

Yet another advantage of the subject matter described herein is that the probiotic substance provides gastric protection and a release mechanism of the probiotics along the intestinal tract at their site of action.

Yet another advantage of the subject matter described herein is that it provides a suitable delivery vehicle for further functional ingredients, in particular non-digestible sugars, natural proteins and prebiotic fibers, which in turn may improve the physico-chemical characteristics of the probiotic substance, as described herein.

BRIEF SUMMARY OF THE SEVERAL VIEWS OF THE DRAWINGS

FIG. 1 is a table that shows drying loss after vacuum drying of *L. rhamnosus* probiotic in the MicroMatrix product described in Example 1.

FIG. 2 is a graph that illustrates storage stability (recovered cfu/g {colony-forming units per gram} versus storage time) of dry *L. rhamnosus* probiotic substance stored at 40° C. and 33% relative humidity.

FIG. 3 is a bar chart that illustrates gastric stability (recovered cfu/g) of probiotic substances incubated in simulated gastric juice (pH=1.2) at 37° C. for 2 hours.

FIG. 4 is an image of examples of probiotic "chips" produced as described herein.

DETAILED DESCRIPTION

The disclosure relates to food products including a probiotic component.

The present disclosure relates to a food or feed product comprising viable microorganisms, a mixture that protects probiotics against high temperature, humidity and low pH, the use of the probiotic substance in a food product and a process for obtaining a probiotic substance to supplement food or feed products. The disclosure further relates to a food product comprising the probiotic substance.

The subject matter described herein relates generally to a composition for preserving probiotic microorganisms, and to the production and drying methods of the substance. More specifically, the subject matter described herein includes a dry probiotic substance with long-term shelf life under high temperature and humid conditions.

Definitions

As used herein, each of the following terms has the meaning associated with it in this section.

The term "food product" is intended to encompass any consumable matter of either plant or animal origin or of synthetic sources that contain a body of nutrients such as a carbohydrate, protein, fat vitamin, mineral, etc. The product is intended for the consumption by humans or by animals, such as domesticated animals, for example cattle, horses, pigs, sheep, goats, and the like. Pets such as dogs, cats, rabbits, guinea pigs, mice, rats, birds (for example chickens or parrots), reptiles and fish (for example salmon, tilapia or goldfish) and crustaceans (for example shrimp). Preferably, the subject matter described herein includes standard food products pelleted feeds, and pet food (for example a snack bar, crunchy treat, cereal bar, snack, biscuit, pet chew, pet food, and pelleted or flaked feed for aquatic animals).

The word "probiotic" is intended to refer to any consumable microorganism owing to any beneficial effect it may have on its consumer.

The term "probiotic substance" is a dry consumable substance in any shape or form that contains probiotics. More specifically, a probiotic substance comprises live probiotics embedded in a matrix of sugars, proteins and polysaccharides. Hence, it may be a food product on its own.

The term "micro-matrix" particles may assume any dry powder form of the probiotic substance. The micro-matrix particles may serve as a carrier for the probiotics and comprise a size from 10 micron up to 2000 micron.

The term "flake or treat" is not intended to refer to specific form or shape of the probiotic substance. A flake or treat may assume any form obtained by molding shaping or slicing a hydrogel. For example, a flake or treat may have the form of a sphere, cube, pyramid, tablet, cereal or any complex three-dimensional form that comprise a size of at least 2 millimeters. For example, if the treats are used as a probiotic delivery system for pet-food, they may have the form of bones, rods, rings or other kibble fauns.

The word "hydrogel" may refer to any moist food-grade substance that has the property of a solid or viscous gel. A hydrogel, either anionic or cationic, can be formed by one or more hydrophilic polymers, polysaccharides, gums, resins, or hydrolyzed proteins, either alone or in combination, in which the microorganisms are disposed. Preferably, the hydrogel compounds include agarose, alginate, chitosan or any other compound, which preferably can present characteristics of a solid gel.

Detailed Description

In order to prepare the probiotic substance as described herein, a single or a mixture of several micro-organisms may be selected. As a probiotic micro-organism, any micro-organism may be selected. Preferably, a micro-organism exerting beneficial effects on health and welfare on humans or animals is used.

Examples of suitable probiotic micro-organisms include yeasts such as *Saccharomyces cereviseae*, molds such as *Aspergillus, Rhizopus, Mucor*, and *Penicillium*, bacteria such as the genera *Bifidobacterium, Clostridium, Bacillus* and *Lactobacillus*. Specific examples of suitable probiotic microorganisms are: *Aspergillus niger, A. oryzae, Bacillus coagulans, B. lentus, B, licheniformis, B, mesentericus, B. pumilus, B, subtilis, B. natto, Bifidobacterium adolescentis, B. animalis, B. breve, B. bifidum, B. infantis, B, lactis, B. longum, B. pseudolongum, B. thermophilum, Candida pintolepesii, Clostridium butyricum, Enterococcus cremoris, E. diacetylactis, Efaecium, E. intermedins, E. lactis, E. muntdi, E. thermophilus, Lactobacillus acidophilus, L. alimentarius, L. amylovorus, L. crispatus, L. brevis, L, case L, curvatus, L. cellobiosus, L. delbrueckii ss, bulgaricus, Lfarciminis, L. fermentum, L. gasseri, L. helveticus, L. lactis, L. plantarum, L. johnsonii, L. reuteri, L. rhamnosus, L. sakei*, and *L. salivarius*.

The probiotic micro-organisms are preferably mixed in a concentrated wet paste form or frozen paste form (for example a probiotic paste of >10% solids) with the other protective substances. Microorganisms may also be mixed, directly after fermentation, with the protective components described herein followed by hydrogel formation and a drying process thereafter. For example, probiotic micro-organisms are mixed with the protective materials such as a saccharide, for example trehalose, sucrose, lactose or maltodextrin, a protein, for example egg albumen, soy protein isolate or hydrolysate either alone or in combination and a polysaccharide, for example, agarose, alginate or chitosan either alone or in combination. A hydrogel is then foamed in a desired shape and size or sliced after hardening the gel according to established procedures known to persons skilled in the art. If micro-matrix particles are required, then the hydrogel can be sliced or extruded and then dried using a variety of drying techniques, for example fluidized bed drying, freeze drying, air drying, convention oven drying or another adequate drying process. The dry probiotic substance is then ground and sieved to preferred sizes. If flakes or treats are required, then the molded or otherwise pre-shaped or sliced hydrogel is preferably dried in a vacuum drier or freeze drier at a temperature above the freezing point of the hydrogel. The pre-shaped dried flake or treat is then ready for packaging alone or in combination with other food products.

Preferably, the probiotic substance comprises significant amounts of the protective composition, in which the microorganisms are embedded. Preferably, the probiotic substance comprises, in percent by weight of total dry matter, 1-50%, preferably 5-25%, more preferably 10-20% of probiotic microorganisms in the protective composition.

In one embodiment, the probiotic substance described herein comprises $10^6$ to $10^{12}$ viable micro-organisms (cfu) per gram dry weight. Preferably, it comprises $10^7$ to $10^{11}$ cfu per gram dry weight.

In another embodiment, the dried probiotic substance is characterized by a water activity below 0.2. Preferably, the water activity is below 0.1, for example, the water activity is in the range of 0.01 to 0.09.

The probiotic substance in accordance with a preferred embodiment comprises of sugar, proteins and polysaccharides. Wherein the protein is selected from natural proteins including albumen, arginine/lysine polypeptide, collagen and hydrolyzed collagen, gelatin and hydrolyzed gelatin, glycoproteins, milk protein, casein, whey protein, serum albumin, meat, fish, seafood, poultry, egg proteins, silk, soybean, corn, peanut, cottonseed, sunflower, pea, wheat protein, wheat germ protein, gluten-protein, zein and any isolate or hydrolyzed of any vegetable protein, and the like.

Preferably, the polysaccharide components of the probiotic substance may be selected in a way that a formation of a solid gel is possible. Generally, this may be achieved by cross linking the polysaccharide (for example by mixing divalent cations with alginate or by cooling the gel (for example agarose).

Additional functional ingredients may be selected to provide further benefits to the probiotic substance described herein. For example fructo-oligosaccharides (FOS) and polyfructoses, for example, inulin, pectin, 6-glucans, resistant starches, for example high amylose starch, dextrans, acacia gum, guar and locust bean gum, agar, carrageenans, xanthan and maltodextrins, and mixtures thereof. Additional functional ingredients may also comprise trace elements, minerals, vitamins, antioxidants, sterols, antioxidants and/or other functional molecules. However, the effect of any additional components on the protective characters of the probiotic substance should be evaluated first. Examples of vitamins and/or antioxidants are carotenoids, such as lycopene, beta-carotene, lutein, xanthophylls, vitamin A, tocopherols, vitamin C, and mixtures thereof.

Since one of the objectives of the compositions and processes described herein is to add the probiotic substance to a food product, it is an advantage that the probiotic substance may be shaped like the desired food product. For example, if the probiotic substance is to be added to a pet food, the probiotic substance may be shaped like a pellet, kibble or bone. Accordingly, if the probiotic substance is added to breakfast-cereals, it may be shaped like cereals. Or, the probiotic substance may be added to a snack as chips. Additionally, the probiotic substance may be added with flavors that used to prepare the food product.

In one embodiment, the probiotic substance may be coaled with a moisture barrier component. In principle, any foodgrade substance having water repelling or impermeable properties may be selected. Suitable moisture barriers may be, for example, waxes (paraffin wax, beeswax, carnauba wax, candellila wax, microcrystalline wax, rice bran wax, shellac, lanolin, hydrogenated castor oil, jojoba oil), fatty acids (for example, oleic acid, stearic acid, palmitic acid, lauric acid), monoglycerides, diglycerides and triglycerides (for example, MCT oil, triglycerides based on coconut/palm kernel oil), vegetable oils and fats (for example, rapeseed, sesame, cornseed, nut, cottonseed, peanut, sunflower, linseed, olive, soy bean, cocoa butter), hydrogenated or hardened vegetable oils and fats, oils and fats of animal origin (for example, beef, poultry, pork, for example, beef tallow, lard and fish oil), hydrogenated or hardened oils and fats of animal origin, dairy fats (for example, milkfat, butterfat), proteins (for example, gluten, zein, sodium and calcium casemate), phospholipids (for example, lecithin), carbohydrates, for example, cellulose and cellulose derivatives (for example, hydroxypropyl methylcellulose, ethylcellulose, methylcellulose, carboxymethyl cellulose), carrageenans, sorbitan esters (for example, monooleate, -palmitate, -stearate, trioleate) and mineral oils and fats (for example, paraffin).

The preparation of the probiotic substance after selection of (the probiotic microorganism and further components of the protecting matrix may be performed in any suitable way. A few principle steps of preparation of the probiotic substance may usually comprise the steps; concentrating the probiotic yield from a fermentor to a solid content of at least 10% and cfu counts of at least 5×10 cfu/g paste, wet mixing of the probiotic concentrate with the other protective components, hydrogel formation in a desirable shape, drying and packaging. If probiotic micro matrix particles are required then a grinding and sieving steps are added. If additional moisture barrier coating is required then the dry probiotic substance is coated immediately after the completion of the drying step.

Most of these steps, for example "wet mixing" and "drying", may be subdivided, for example "mixing only few of the ingredients, drying them by one drying method, adding other ingredients to the mixture, mixing, and drying again with the same or different drying method.

For example, a wet mix of the micro-organisms and further components, is prepared by mixing all components in water, the slurry is then poured into molds of a desired shape and let to harden by adding a cross-linking chemical or by cooling the slurry, or hardening the gel slurry first and then slicing, chopping or shaping the hydrogel to a desired shape. Then the molded chopped, or shaped hydrogel may be dried to water activity ($A_W$) below 0.2, preferably below 0.1. Possible drying processes include air dryers or convection ovens, belt dryers, vacuum dryers, fluidized bed dryers, rotary dryers, just to mention a few. Alternatively, all components can be added to the wet probiotic concentrate without the addition of more water. For example, trehalose is first mixed in a probiotic concentrate (that contains about 10-20% solids), and then egg albumen or soy protein isolate and polysaccharides are added. Additional amount of proteins may be added to obtain semi-dry powder that can be further granulated, dried and sieved to specific size range of probiotic granulated-matrix particles.

The preparation of probiotic substances in a shape of crispy flakes or treats involves a vacuum drying process where the product temperature is set above the freezing temperature of the probiotic substance. In general, vacuum drying are performed in two steps. The first step involves moderately reduced pressure (ca. 5000 mTORR) and high shelf temperatures (ca. 5-50° C.), whereas the second step involves lower pressures (e.g., higher vacuum such as not more than 100 mTORR) while maintaining higher shelf temperature (up to about 50° C.).

This process can be achieved using a programmable control system for vacuum pressure and product temperature. The vacuum and temperature conditions for the first drying step is adjusted empirically according to the size of the drier, heat transfer capacity, and the product load, but the goal is to keep the product above its freezing temperature while maximizing the water evaporation rate. In one embodiment, the temperature is initially maintained at about 40° C. for about 6 hours, until most of the free water evaporated from the material, followed by gradually increasing the vacuum from the initial set up of ca. 5000 mTORR up to 100 mTORR, then maintaining these drying conditions until the water activity of the probiotic substance is sufficiently low (see values given above). Following this protocol, the drying procedure is completed within 24 hours without substantially compromising the probiotic viability. The large surface area of the shaped, sliced or chopped hydrogel greatly increases evaporation rate without the need to "boil" or foam the product in thin layers as indicated by other disclosures, thus eliminating inconsistent drying conditions and splattering of the foamed product solution within the vacuum chamber. Additionally, the disclosed composition and method of drying enable higher loading capacity of product in the vacuum or freeze drier as compared to other drying methods of materials with high sugar contents (i.e., foam formation).

The flake or treat may have the shapes as indicated above and be of any suitable, adequate or desired form. For example, they may have the form of spheres, cubes, pyramids, tablets, long tubes or any complex three-dimensional form. Furthermore they may have a form that corresponds to the food product to which they are added. For example, if the treats are added to a pet food for dogs, they may have the form of bones, animals, cats or other forms that fit with the food product.

In still another embodiment, the dried probiotic substance may be coated to further protect the micro-organism from deleterious effect of subsequent absorption of water during the shelf-life of the food product. The coating may be done by any suitable coating technique, for example, spraying, melt or solvent coating equipment, fluidized bed coater, drum coater or pan coater, just to mention a few.

The amount of coating depends on the size and form of the probiotic substance. Generally, the amount of coating compound is higher for smaller size particles. Accordingly, the amount of the coating compound for probiotic micro-matrix or granulated matrix particles is from 10 to 50%, more preferably 20 to 40% of the total weight of the coated probiotic particles. The amount of the coating compound for flake or treat shapes probiotic substance is from 5 to 30%, more preferably 10 to 20% of the total weight of the coated probiotic treat. It is also understood that, for the purposes described herein, the coating process can result in a single layer of one compound or a mixture of compounds or to multiple layers of one or more compounds.

In a further embodiment, the probiotic substance provides gastric protection to the probiotic microorganisms. While the sugar component in the protective matrix immediately dissolves upon intact with the animal stomach juice, the polysaccharide protein matrix retains its form in the acid environment, thereby protecting the embedded microorganisms from digestive incursions. The matrix, however, slowly disintegrate in the alkali-phosphate environment of the gut and hence liberating the intact probiotic microorganisms to colonize the animal gut.

In additional embodiment, the probiotic product may be used exclusively as an entire food product, for example as a treat or a supplement, or added and mixed with a food product, or be used in its powder form to coat an existing food product, for example for top-coating pelleted or extruded feeds.

The following examples are given by way of illustration only and in no way should be construed as limiting the subject matter of the present application.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Preparation of Dry and Stable Probiotic Substance

Basic Formulation 300 g of trehalose (Cargill Minneapolis, Minn.) was added to 1000 ml water and allowed to completely dissolve. Soy protein isolate (100 g, Feam Natural Foods, Mequon, Wis.) and soy hydrolysate (20 g, Sigma-Aldrich, St. Louis, Mo.) were added under vigorous mixing using a standard household blender. Sodium alginate (20 g) was then mixed into the slurry and allowed to cool down to room temperature. *Lactobacillus paracasei* (100 g frozen concentrate direct from fermentation harvest) was then added to the slurry under vigorous mixing until a smooth and uniform thick gel was achieved. The composition of the hydrogel is provided in Table 1.

TABLE 1

| Hydrogel composition (g dry weight/100 ml water) | |
|---|---|
| Trehalose | 30 g |
| Soy protein isolate | 10 g |
| Soy protein, hydrolysate | 2 g |
| Sodium Alginate | 2 g |
| *L. paracasei* paste | 10 g |

Production of Probiotic Flakes

Five grams of calcium phosphate dibasic was mixed in the basic formula followed by 5 g of gluconolactone and the slurry was allowed to harden (solid hydrogel) at room temperature over the next 4 hours. The firm gel was sliced to thin and long leafs, through cheese grinder. The thin leafs were loaded on a tray (13×10 inch) and placed in a freeze drier (Virtis Advantage, Virtis, Gardiner, N.Y.). The condenser was set to −70° C. and shelf temperature was set to +40° C. The vacuum was then initiated and controlled at about 5000 mTORR with an external vacuum controller (Thyr-Cont, Electronic, GmbH). The wet product temperature fell to and stabilized at about −5 to 0° C. The chamber atmospheric pressure was then gradually decreased as the product temperature started to warm up (measured by a pair of temperature sensors plugged in the wet material), until rail vacuum pressure of 100 mTORR was established. Over this time period of increasing vacuum, the product temperature was carefully maintained between −5° C. and +5° C. Twenty four hours after establishing full vacuum, the dried product was taken out of the freeze drier. The water activity ($A_W$) of the probiotic substance after the drying protocol was 0.05 (Measured by HygroPalm Awl, Rotonic Huntington, N.Y.).

Production of Probiotic Treats

The above basic formulation slurry was poured into muffin plates having molds of small hearts or stars shapes and allowed to harden (solid hydrogel) at room temperature over the next 4 hours. The plates containing the molded hydrogel was placed in a freeze drier and allowed to dry as described above.

Production of Probiotic Micro Matrix Particles

The above basic formula was extruded or dripped into a 1000 ml bath (held at 0-5° C.) containing 5 g $CaCl_2$ and 300 g trehalose using a syringe equipped with 18 G needle. The $CaCl_2$ bath was gently stirred while injecting the slurry. The matrix strings or drops were allowed to cross-link for 30 minutes and then harvested and blotted on paper towel. The strings or drops were first dried in a convection oven at 35 degree C. until water activity of the material reduced to 0.5 then they were transferred to a freeze drier for final drying of about 24 hours. The dry drops or strings (Aw=0.06) then ground to fine powder using standard coffee grinder and sieved through 50-250 micron screens.

Alternatively, probiotic micromatrix particles can be obtained by grinding and sieving already dried probiotic flakes or treats as described above.

Production of Probiotic Granulated Matrix Particles 600 g of trehalose (Cargill Minneapolis, Minn.) was added to 1200 ml of concentrated paste of *Lactobacillus acidophilus* (20% solid concentrate direct from fermentation harvest) and allowed to completely dissolve. Soy protein isolate (200 g, Fearn Natural Foods, Mequon, Wis.) and soy hydrolysate (20 g, Sigma-Aldrich, St. Louis, Mo.) were added under vigorous mixing using a standard household mixer. Sodium alginate (40 g) was then mixed into the slurry and allowed to cool down to room temperature. After a smooth, thick and uniform gel was achieved, 5 g of calcium carbonate was added. Immediately after, 1000 g of egg white (Sigma-Aldrich, St. Louis, Mo.) was slowly added under vigorous mixing until a semi-moist free flowing powder was obtained. The granulated probiotic powder was dried in a convection oven at 40 degree C. for 2 h followed by a vacuum drying for 24 h to obtain dry (Aw<0.06) granulated matrix particles. The granulated particles can be sieved to specific size range through a series of 50-500 micron sieves. The composition of the probiotic granulated matrix particles is provided in Table 2.

TABLE 2

| Hydrogel composition | |
|---|---|
| Trehalose | 60 g |
| Soy protein isolate | 20 g |
| Soy protein hydrolysate | 2 g |
| Sodium Alginate | 4 g |
| *L. acidophilus* paste | 120 g |
| Egg white | 100 g |

Recovery of *L. Rhamnosus* after Production of Dry Micromatrix Particles.

*L. rhamnosus* micromatrix particles were produced as described above. CFU counts of concentrated *L. rhamnosus* after harvesting from a fermentor and centrifuging were $5 \times 10^{10}$/g paste and solid content was 24%. After mixing the probiotic with all protective components, forming hydrogel, chopping the hydrogel to small threads, drying in a freeze-drier for 24 h, grinding and sieving to particle size between 50-250 micron, the CFU counts were $9.4 \times 10^9$/g dry micromatrix. This represents a loss of 0.28 log of probiotic activity during the manufacturing process (as illustrated in FIG. 1).

Stability of *L. rhamnosus* in 40° C. at 33% Relative Humidity (RH).

*L. rhamnosus* probiotic micromatrix particles were prepared and dried as described above. The dried probiotic particles were placed in temperature and humidity control incubators set at 40° C. and 33% relative humidity for 4 weeks. Viabilities of bacteria dried in only in 10% trehalose solution or in the protective mixture described herein were measured on a weekly interval. FIG. 2 shows that the protective mixture provided a significant protection to that of trehalose alone dried bacteria.

Stability of *L. Rhamnosus* Micromatrix Particles in Simulated Gastric Juices

Micromatrix particles (50-250 micron) containing either *L. rhamnosus* (LGG), *L. acidophilus* (LA5) or *L. paracase* (LPC) were prepared and dried as described above. The micromatrix particles were then exposed for 2 hours to simulated gastric juice (full stomach—12% non fat skim milk, 2% glucose, 1% yeast extract and 0.05% cysteine; pH 2; or empty stomach—0.32% pepsin, 0.2% sodium chloride, pH 1.2). Bacterial viabilities were recorded before and after the exposure to the simulated gastric juices. FIG. 3 demonstrate a significant protection of the probiotic bacteria in the micromatrix substance in simulated gastric conditions.

Coating of the Probiotic Substances

Probiotic substances were coated with a fat-based moisture barrier (a mixture of 20% jojoba oil, 70% cocoa butter and 10% beeswax) in a drum tumbler at a temperature of 40 degrees C. The moisture barrier was sprayed on using a spraying nozzle while the dry material is agitated in the drum tumbler to ensure homogeneous coating. The total amount of coating was about 20% (of the uncoated probiotic substances) for probiotic flakes and treats, and 40-50% for probiotic micromatrix particles.

Example 2

Preparation of Probiotic Pet Food

Pet food for dogs that is commercially available was first dried in a convection oven to a water activity of 0.1, and then coated with probiotic micromatrix particles in a drum tumbler. The pellets were first sprayed with about 5% of fat-based moisture barrier (a mixture of 40% chicken fat, 40% cocoa butter and 20% beeswax), then mixed with the micro matrix particles (usually 0.1-0.5% of total pet food that provides a dosage of $10^8$ CFU/g) and finally sprayed with additional coat of the fat-based moisture barrier. The total amount of coating was about 15% (of the pet food). Coating time was about 30 minutes.

Example 3

Preparation of Fish Feed with Several Probiotic Micro-Organisms

Pelleted feed for fish was prepared with a mixture of several probiotics. Probiotic micromatrix particles containing a mixture of *L. rhamnosus, L. acidophilus* and *Bifidobacterium lactis* (DSM 20215) were prepared as described in Example 1. Fish feed that is commercially available was first dried in a convection oven to a water activity of 0.1, and then coaled with probiotics micromatrix particles in a drum tumbler. The pellets were first sprayed with about 5% of fat-based moisture barrier (a mixture of 40% fish oil, 40% cocoa butter and 20% beeswax), then mixed with the micro matrix particles (usually 0.1-0.5% of total fish feed that provides a dosage of $10^7$ cfu/g) and finally sprayed with additional coat of the fat-based moisture barrier. The total amount of coating was about 10% (of the fish feed).

Example 4

Preparation of Probiotic "Chips" (as Shown in FIG. 4)

Probiotic chips were prepared with a mixture of *L. rhamnosus* and *L. acidophilus* as described in Example 1. The basic formula was added with about 1-2% of probiotic pastes instead of the standard 10-20% load. Five gram of calcium phosphate dibasic was mixed in the basic formula followed by 5 g of gluconolactone and the slurry was pored into long plastic tubes of 1-inch diameter and allowed to harden (solid hydrogel) at room temperature over the next 4 hours. The firm "hot-dog" shaped gel was sliced to thin discs, loaded on a tray (13×10 inch) and placed in a freeze drier and a drying procedure applied as described in Example#1. The dried probiotic chips product was taken out of the freeze drier and packed under nitrogen in small aluminum foiled packs that provide tasty and crispy treat containing an effective dose of $10^8$ CFU/per serving. FIG. 4 shows an example of probiotic chips containing $10^8$ CFU/serving of *rhamnosus* produced as described herein.

Example 5

Preparation of Probiotic Cereals

Breakfast cereal that is commercially available was first dried in a convection oven to a water activity of 0.1. Probiotic chips containing a standard 10-20% load of probiotics were produced and further coated with a moisture barrier as described in Examples 1 and 4. The cereals were then mixed with 0.1-0.5% probiotic chips (to provide a dosage of $10^8$ cfu/g).

Example 6

Alternative Delivery Forms of Probiotic Matrix Substances in the Lid of a Container or a Bottle of Beverage Drink In general, all forms of the probiotic substances produced as in Example 1 or Example 4 work similarly well, confirming the high versatility of usage and application of the materials. The probiotic substances produced as described herein can be provided in small bags or paper "stick" packaging or in any other manner along with an edible food product. The dry micromatrix particles or chips may also be provided in the lid of a yogurt container or a bottle of beverage drink to be mixed with the liquid food product for consumption.

References

The following references are referred to herein.

Bronshtein, V. (WO2005117962). Preservation by vaporization (2005).

Cavadini, C, Ballevre, O. and Gaier, H. (EP 0 862 863). Cereal product containing probiotics.

Crowe, J. H., Carpenter, J. F. and Crowe, L. M. (1998). "The role of vitrification in anhydrobiosis. Review." Arum Rev Physiol. 60: 73-103.

Farber, M. and Farber, J. (WO 03/088755). Delivery systems for functional ingredients (2003).

Giffard, C J. and Kendall, P. (US 2005/0079244). Foodstuff (2005).

Hughes, V X. and Hillier, S. L. (1990). "Microbiologic characteristics of *Lactobacillus* products used for colonization of the vagina." Obstet Gynecol. 75: 244-248.

Kenneth, A. M. and Liegh, B. T. (U.S. Pat. No. 6,900,173). Perioperative multivitamin protein bar for use in preparing an individual for fast surgical recovery (2005).

Ko, S. T. and Ping, Y. A. T. (WO 02/058735). Methods of preparing biological materials and preparation produced using the same.

McGrath, S. and Mchale, A. P. (EP 1382241). Storage and delivery of microorganisms (2004).

Porubcan, R. S. (US 2004/0175389). Formulations to increase in vivo survival of probiotic bacteria and extend their shelf-life (2004).

Shah, N. P. (2000). "Probiotic bacteria: selective enumeration and survival in dairy foods." Journal of Dairy Science 83: 894-907.

Ubbink, J. B., Zammaretti, P. S. and Cavadini, C. (US 2005/0153018). Probiotic delivery system (2005).

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A probiotic substance comprising particles, each of which comprises viable probiotic bacteria embedded in a dried matrix, wherein the dried matrix is a mixture comprising:
- at least one sugar, wherein the at least one sugar comprises trehalose, wherein the total amount of sugar in the dried matrix is from about 20% to about 60% by weight of the dried matrix;
- at least one protein, wherein the total amount of protein in the dried matrix is from about 2% to about 20% by weight of the dried matrix and wherein the at least one protein comprises egg white, soy protein isolate, soy protein hydrolysate or a combination thereof;
- at least one polysaccharide, wherein the at least one polysaccharide comprises an alginate; and
- optionally additional functional ingredients;
- wherein the total amount of polysaccharide in the dried matrix is from about 0.5% to about 5% by weight of the dried matrix;
- wherein the probiotic substance is prepared by a process comprising:
  a) mixing the probiotic bacteria with the at least one sugar, the at least one protein, the at least one polysaccharide and optionally the additional functional ingredients to obtain a slurry, and optionally adding a crosslinking chemical to form a gel in a desired shape and form; and
  b) vacuum drying the slurry or the gel, wherein the vacuum drying comprises setting the temperature of the probiotic substance above its freezing temperature and vacuum drying at reduced pressure at a shelf temperature of from 5-50° C. and then gradually decreasing the pressure, as the temperature of the probiotic substance increases, down to a pressure of about 100 mTorr while maintaining the shelf temperature from 5-50° C.

2. The probiotic substance according to claim 1, wherein the crosslinking chemical is added.

3. The probiotic substance according to claim 2, wherein the loss of probiotic activity upon exposure to simulated gastric juice (pH=1.2) at 37° C. for 2 hours is at least 1.5log less than for probiotic material not embedded in the dried matrix.

4. The probiotic substance according to claim 1, wherein the dried matrix has a water activity below 0.2.

5. The probiotic substance according to claim 1, comprising $10^5$ to $10^{14}$ viable micro-organisms per gram of probiotic substance.

6. The probiotic substance according to claim 1, wherein the loss of probiotic activity during the process is less than 1.87 log.

7. The probiotic substance according to claim 1, wherein the probiotic substance is coated with a moisture barrier comprising a food-grade substance having water-repelling or water-impermeable properties.

8. The probiotic substance according to claim 7, wherein the moisture barrier is selected from the group consisting of oils, waxes and fats.

9. A human food product comprising a foodstuff and one or several probiotic substances according to claim 1.

10. The human food product of claim 9, wherein the food product is in a moist or dry form.

11. The human food product of claim 9, wherein the food product is in a powdered, particulate, pellet, tablet, bar, capsule, hydrogel or liquid form.

12. The human food product of claim 9, wherein the food product is a cereal, a treat, a nutraceutical food additive or a pharmaceutical food additive.

13. An animal feed product comprising a feedstuff and one or several probiotic substances according to claim 1.

14. The animal feed product of claim 13, wherein the feed product is in a moist or dry form.

15. The animal feed product of claim 13, wherein the feed product is in powdered, particulate, pellet, tablet, capsule, hydrogel or liquid form.

16. The animal feed product of claim 13, wherein the feed product is a treat, nutraceutical feed additive or a pharmaceutical feed additive.

17. The animal feed product of claim 13, wherein the animal feed is terrestrial or aquatic animal feed.

18. The probiotic substance according to claim 1, wherein the total amount of the sugar, protein and polysaccharide is from about 50% to about 85% by weight of the dried matrix.

19. A probiotic substance comprising particles, each of which comprises viable probiotic bacteria embedded in a dried matrix, wherein the dried matrix is a mixture comprising:
- at least one sugar, wherein the at least one sugar comprises trehalose, wherein the total amount of sugar in the dried matrix is from about 20% to about 60% by weight of the dried matrix;
- at least one protein, wherein the total amount of protein in the dried matrix is from about 2% to about 20% by weight of the dried matrix and wherein the at least one protein comprises egg white, soy protein isolate, soy protein hydrolysate or a combination thereof;
- at least one polysaccharide, wherein the at least one polysaccharide comprises an alginate; and
- optionally additional functional ingredients;
- wherein the total amount of polysaccharide in the dried matrix is from about 0.5% to about 5% by weight of the dried matrix; and
- wherein the probiotic substance has probiotic activity representing a loss of less than 1.87 log relative to the activity of the probiotic bacteria from which the probiotic substance was prepared.

* * * * *